US007039810B1

(12) United States Patent
Nichols

(10) Patent No.: US 7,039,810 B1
(45) Date of Patent: May 2, 2006

(54) METHOD AND APPARATUS TO SECURE DATA TRANSFER FROM MEDICAL DEVICE SYSTEMS

(75) Inventor: Timothy J. Nichols, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/431,881

(22) Filed: Nov. 2, 1999

(51) Int. Cl.
H04L 9/00 (2006.01)
A61N 1/08 (2006.01)

(52) U.S. Cl. ............... 713/182; 713/193; 607/60
(58) Field of Classification Search ........... 713/150, 713/176, 179, 182, 193; 380/255, 270; 607/59, 607/60
See application file for complete search history.

(56) References Cited

U.S. PATENT DOCUMENTS

| | | | | |
|---|---|---|---|---|
| 4,842,531 | A | 6/1989 | Takemura | 439/165 |
| 5,321,618 | A | 6/1994 | Gessman | 364/413.06 |
| 5,345,362 | A | 9/1994 | Winkler | 361/681 |
| 5,764,476 | A | 6/1998 | Ohgami et al. | 361/683 |
| 5,800,473 | A * | 9/1998 | Faisandier | 607/59 |
| 6,026,165 | A * | 2/2000 | Marino et al. | 380/273 |
| 6,249,705 | B1 * | 6/2001 | Snell | 607/59 |
| 6,477,424 | B1 * | 11/2002 | Thompson et al. | 607/60 |

FOREIGN PATENT DOCUMENTS

WO    WO 99/14882    3/1999

OTHER PUBLICATIONS

"A Multimedia-Based Medical Database Network System for Special Clinical Procedures in Healthcare Delivery," Krishnan, IEEE/EMBS conference—Nov. 2, 1997.
"Making Sense of Encrypted Communications," Varhol, Computer Design, Jan. 1998.
"Cardio Thoracic System in Use at Northwest Hospital," University of Washington.
"The Next Generation in Healthcare Information Management," Healtheon Company.

* cited by examiner

Primary Examiner—Matthew Smithers
(74) Attorney, Agent, or Firm—Daniel G. Chapik; Girma Walde-Michael

(57) ABSTRACT

Sensitive data such as patient records are securely transferred between a programmer and a data encryption. A database residing on the programmer contains patient information obtained by at least one implantable medical device. A key source provides the programmer with a first key and the remote expert data center with a second key to be used in the encryption/decryption process. An encryption engine residing within the programmer encrypts the sensitive patient information contained within the database, using the first key. The programmer transmits the encrypted patient information to the remote expert data center via a data communications system such as a public network. A decryption engine residing within the remote expert data center decrypts the encrypted sensitive patient information using the second key.

69 Claims, 8 Drawing Sheets

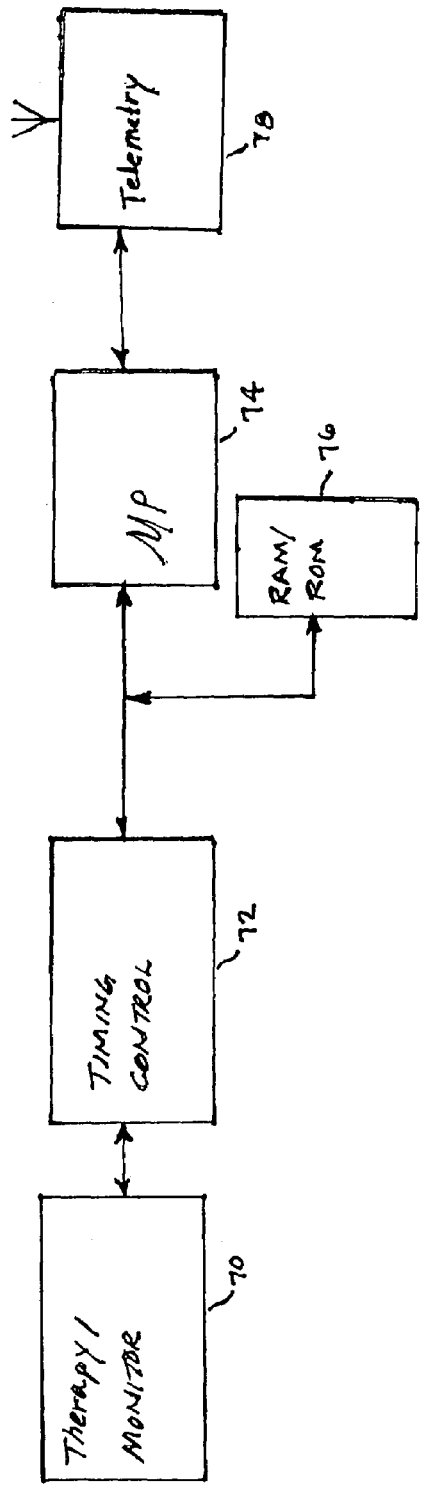
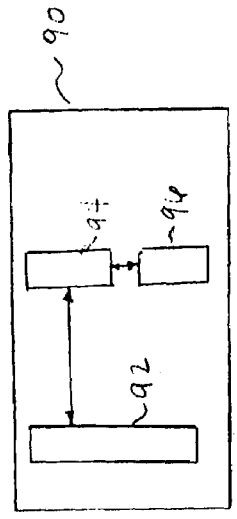
FIG - 2
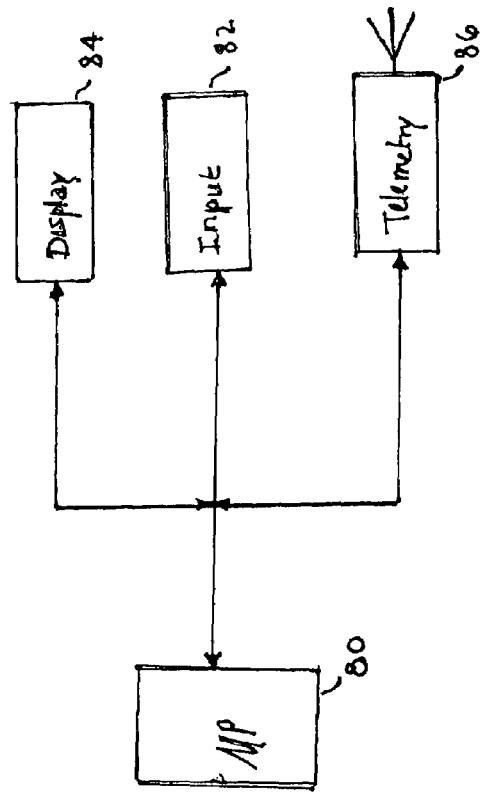
FIG - 3A
FIG - 3B

METHOD AND APPARATUS TO SECURE DATA TRANSFER FROM MEDICAL DEVICE SYSTEMS

THE FIELD OF THE INVENTION

The present invention relates generally to medical device systems. Specifically, the invention pertains to a remote bi-directional communications with one or more programmable devices, that are associated with implantable medical devices (IMDs). Generally, the invention relates to an integrated system and method of bi-directional telecommunications between a web-based expert data center and at least one programmer, utilizing various types of network platforms and architecture to implement, in the programmer, distance-based troubleshooting, maintenance, upgrade, information and administrative services thereby providing an economical and highly interactive system for therapy and clinical care. More specifically, the invention relates to an apparatus and method for securely transferring sensitive information, such as patient information, between a programmer and a remote data center using encryption methods and structure implemented in both hardware and software systems to prevent abuse.

BACKGROUND OF THE INVENTION

A technology-based health care system that fully integrates the technical and social aspects of patient care and therapy should be able to flawlessly connect the client with care providers irrespective of separation distance or location of the participants. While clinicians will continue to treat patients in accordance with accepted modern medical practice, developments in communications technology are making it ever more possible to provide medical services in a time and place independent manner.

Prior art methods of clinical services are generally limited to in-hospital operations. For example, if a physician needs to review the performance parameters of an implantable device in a patient, it is likely that the patient has to go to the clinic. Further, if the medical conditions of a patient with an implantable device warrant a continuous monitoring or adjustment of the device, the patient would have to stay in a hospital indefinitely. Such a continued treatment plan poses both economic and social problems. Under the exemplary scenario, as the segment of the population with implanted medical devices increases many more hospitals/clinics including service personnel will be needed to provide in-hospital service for the patients, thus escalating the cost of healthcare. Additionally the patients will be unduly restricted and inconvenienced by the need to either stay in the hospital or make very frequent visits to a clinic.

Yet another condition of the prior art practice requires that a patient visit a clinic center for occasional retrieval of data from the implanted device to assess the operations of the device and gather patient history for both clinical and research purposes. Depending on the frequency of data collection this procedure may pose a serious difficulty and inconvenience for patients who live in rural areas or have limited mobility. Similarly, in the event a need arises to upgrade the software of an implantable medical device, the patient will be required to come into the clinic or hospital to have the upgrade installed.

Further, in medical practice it is an industry-wide standard to keep an accurate record of past and present procedures relating to an IMD. Generally, a report should be generated each time a medical component such as a programmer and/or analyzer is connected to the IMD. Various information should be contained in the report including an identification of all the medical components used during a procedure. Specifically, all peripheral and major devices that are used in down linking to the IMD need to be reported. Presently, there is no automated system for providing an automated report of all the major components used in a procedure involving communications with an IMD. The current practice is for a medical person to physically record or enter data related to the devices used in the down linking procedure. One of the limitations of this procedure is the fact that it is error prone and often requires rechecking of the data to verify accuracy. Further, current practice does not allow secure patient data transfer across communicating media systems.

Protecting the safety and privacy of patient medical information has become a growing concern of health care organizations. The explosive growth of the internet and distributed computing environments is largely responsible for connecting previously disconnected remote computing platforms of health care providers. The cost of establishing and maintaining proprietary data networks between remotely communicating computers and data centers is very expensive. Thus health care organizations increasingly rely on unsecure "public" networks, such as the internet or public telephone systems to connect remote computing platforms. As a result, while in transit, sensitive patient medical records are compromised and healthcare providers may be liable to privacy and breach of confidentiality claims. Generally, these risks are not encountered in non-networked computing platforms.

As the sophistication of medical devices increases, health care providers are faced with new challenges in protecting sensitive patient information. Some medical devices are now capable of performing independent data transfers across communications networks to data centers, or to other medical devices. One example of such a medical device is a programmer. Programmers are used to initialize and service various implanted devices. These implanted devices include, for example, neural implants, pacemakers and cardioversion/defibrillator devices. Presently, typical programmers in use by physicians are generally the size and shape of a portable laptop computer. Communication with an implanted device is accomplished through a radio frequency (RF) connection by using an accessory connected to the programmer. The programmer further includes a screen for displaying alphanumeric information, and, optionally, to display graphic information such as an electrogram (EGM) or an electrocardiogram (ECG). The programmer also includes an interface with a printer for printing information, such as the programming parameters set for a particular pacemaker, data logged by the pacemaker for a pre-selected period, or an ECG graph.

Data encryption has been increasingly used to add security and privacy to data, voice and video transmissions across public networks. Encryption involves the translation of data into a secret code. A common method includes the scrambling of bit patterns. To read an encrypted file, a user must have access to a secret key or password to decrypt the data. Unencrypted data is called plain text, while encrypted data is referred to as cipher text. There are two main types of encryption (discussed in more detail below): asymmetric encryption (also called public-key encryption) and symmetric encryption. Encryption algorithms have been available for some time, but only recently have low-cost processors become fast enough to perform encryption and decryption functions in a reasonable amount of time.

Several methods can be used to encrypt data streams, all of which can easily be implemented through software. The simplest of all of the methods is the translation table. Each piece of data (usually 1 byte) is used as an offset within a translation table, and the resulting translated value from within the table is then written into the output stream. The encryption and decryption programs each use a table that translates to and from the encrypted data. Some central processing units (e.g., Intel Corporation's 80×86 series) have an instruction "XLAT" that perform the translation at the hardware level. While the translation table method is very simple and fast, once the translation table is known, the code is broken.

A modification to the translation table method uses two or more tables, based on the position of the bytes within the data stream, or on the data stream itself. Decoding becomes more complex, since the same process must be reversed reliably. By using more than one translation table (i.e., especially when implemented in a "pseudo-random" order), breaking the encryption code becomes considerably more difficult. As an example, one translation method might use translation table "A" on all of the even bytes, and translation table "B" on all of the odd bytes. Unless a potential code breaker knows that there are exactly two tables, even with both source and encrypted data available, the deciphering process is relatively difficult.

Another encryption method, known as data repositioning, reads a buffer of data from the input source, rearranges the order of the bytes, and writes the results to an "out of order" output. The decryption program then reads the output, and puts the "out of order" data back in order.

The most commonly employed (and complex) encryption method involves word/byte rotation and XOR bit masking. Under this method, if words or bytes within a data stream are rotated, using multiple and variable directions and duration of rotations in a reproducible pattern, a stream of data is quickly encoded with a method that is nearly impossible to break. Further, if an "XOR mask" is used in combination with the rotations (i.e., "flipping" the bits in predefined positions from 1 to 0, or 0 to 1), the code breaking process is made even more difficult.

One feature of a good encryption scheme is the ability to specify a "key" or "password", and have the encryption method alter itself such that each "key" or "password" produces a different encrypted output, which requires a unique "key" or "password" to decrypt. Symmetric encryption is a type of encryption where the same key is used to encrypt and decrypt the message. This differs from asymmetric (or public-key) encryption, which uses one key to encrypt a message and another (different) key to decrypt the message.

In a symmetric-key encryption system, two people first agree on a pass phase, such as a phone number or fax number. At the sending end, the encryption software turns the pass phase into a binary number, then uses that binary number (e.g. key) to encrypt all outgoing messages. The mathematical module used for encrypting the message is called the algorithm. The whole system is referred to as a cipher. At the receiving end, each incoming message is decrypted using the same key. The receiver types in the agreed pass phrase, the software converts it to the binary key, and uses the binary key to decrypt the cipher text (i.e., the incoming message). Out of the conversion comes plain text (i.e., the original message in readable form). To summarize, in symmetric-key encryption, the same key is used to encrypt and decrypt. Symmetric key encryption assumes that the sender and receiver have another way to communicate that is also very secure, so that the keys can be distributed safely.

In contrast to symmetric-key encryption, public key encryption uses two different keys—a public key known to everyone and a private or secret key known only to the recipient of the message. As an example, when a sender wishes to send a secure message to the recipient, the sender uses the recipient's public key to encrypt the message. The recipient then uses the recipient's private key to decrypt the message. In public key encryption, the public and private keys are related in such a way that only the public key can be used to encrypt messages and only the corresponding private key can be used to decrypt messages. Moreover, it is virtually impossible to deduce the private key if the public key is known. One difficulty with public-key systems is that the sender needs to know the recipient's public key to encrypt a message.

While encryption safeguards the data transmitted between the sender and the recipient, a digital signature is often employed to validate the authenticity of a communication. The most common use of a digital signature is to verify that a user sending a message is who he/she claims to be. Using the public key encryption method described above, a digital signature can be created by using a private key to encrypt a message digest (i.e., a representation of text in the form of a single string of digits, created using a formula called a one-way hash function). One possible format for a message digest is a 128-bit one-way hash function, similar to an error-checking code used to detect faulty communications. By using 128 bits, there are $2^{128}$ possible combinations, making the message digest computationally too intensive to decipher.

The digital signature can be verified by using the sender's public key to decrypt the signature. Because it is encrypted with the private key, only the originator of the message could have prepared it. And since it is decrypted with the public key, any user can verify that it was sent by the originator. The digital signature can be used in conjunction with a message by first creating the message digest with the sender's private key, attaching the digital signature to the communication, then encrypting both the message and the digital signature with the recipient's public key. The recipient reverses these steps, first decrypting the message with their private key, then decrypting the signature with the public one.

While data encryption and digital signatures have seen increasing use in computer-to-computer data transfers and messaging applications across public networks, these security measures have not been utilized in medical device applications. Until recently, the technology for transferring operational information between programmers used in conjunction with an implantable medical device and a remote data center has proven impracticable, if not impossible. Because of the highly critical nature of the information involved, security and reliability of the transfer is of manifest importance. Medical devices are often widely dispersed across the world, necessitating a common communications medium available to all users of the medical devices across the world, no matter where the medical device is located. The data transmission facility must also be universally available quick, cost effective, and easy to use.

A further limitation of the prior art relates to the management of multiple implantable devices in a single patient. Advances in modem patient therapy and treatment have made it possible to implant a number of devices in a patient. For example, implantable devices such as a defibrillator or a pacer, a neural implant, a drug pump, a separate physiologic monitor and various other implantable devices may be implanted in a single patent. To successfully manage the operations and assess the performance of each device in a patient with multi-implants requires a continuous update and monitoring of the devices. Further, it may be preferred to have an operable communication between the various implants to provide a coordinated clinical therapy to the patient. Thus, there is a need to monitor the performance of the implantable devices on a regular, if not a continuous, basis to ensure optimal patient care. In the absence of other alternatives, this imposes a great burden on the patient if a hospital or clinic is the only center where the necessary frequent follow up, evaluation and adjustment of the medical devices could be made. Moreover, even if feasible the situation would require the establishment of multiple service areas or clinic centers to provide adequate service to the burgeoning number of multi implant patients worldwide. Accordingly, it is vital to have a programmer unit that would connect to a remote expert medical center to provide access to expert systems and import the expertise to a local environment. This approach would enable unencumbered access to the IMD or the patient. Further, the proliferation of patients with multi-implant medical devices worldwide has made it imperative to provide remote services. Thus, frequent use of programmers to communicate with the IMD and provide various remote services, have become an important aspect of patient care as indicated in the disclosures contained in co-pending applications titled "Apparatus and Method for Remote Troubleshooting, Maintenance and Upgrade of Implantable Device Systems," filed on Oct. 26, 1999, Ser. No. 09/426,741, now U.S. Pat. No. 6,442,433; "Tactile Feedback for Indicating Validity of Communication Link with an Implantable Medical Device," filed Oct. 29, 1999, Ser. No. 09/430,708, now U.S. Pat. No. 6,644,321; "Apparatus and Method for Automated Invoicing of Medical Device Systems," filed Oct. 29, 1999, Ser. No. 09/430,208, now U.S. Pat. No. 6,385,593: "Apparatus and Method for Remote Self-Identification of Components in Medical Device Systems," filed Oct. 29, 1999, Ser. No. 09/429,950, now abandoned; and "Apparatus and Method to Automate Remote Software Updates of Medical Device Systems," filed Oct. 29, 1999, Ser. No. 09/429,960, now U.S. Pat. No. 6,363,282, which are all incorporated by reference herein in their entirety.

The prior art provides various types of remote sending and communications with implantable medical devices. One such example is disclosed by Gessman in U.S. Pat. No. 5,321,618 issued. In this disclosure a remote apparatus is adapted to receive commands from and transmit data to a central monitoring facility over telephone communication channels. The remote apparatus includes equipment for acquiring a patient's ECG waveform and transmitting that waveform to the central facility over the telephone communications channels. The remote apparatus also includes a segment, responsive to a command received from the central monitoring facility, for enabling the emission of audio tone signals from the cardioverter defibrillator. The audio tones are detected and sent to the central monitoring facility via the telephone communication channel. The remote apparatus also includes patient alert devices, which are activated by commands received from the central monitoring facility over the telephone communication channel.

One of the many limitations of the apparatus and method disclosed in the Gessman patent is the fact that the segment, which may be construed to be equivalent to a programmer, is not remotely adjustable from the central monitoring device. The segment merely acts as a switching station between the remote apparatus and the central monitoring station. Further, there is no indication of security for the patient data being collected.

An additional example of prior art practice includes a packet-based telemedicine system for communicating information between central monitoring stations and a remote patient monitoring station disclosed in Peifer, WO 99/14882 published 25 Mar., 1999. The disclosure relates to a packet-based telemedicine system for communicating video, voice and medical data between a central monitoring station and a patient that is remotely located with respect to the central monitoring station. The patient monitoring station obtains digital video, voice and medical measurement data from a patient and encapsulates the data in packets and sends the packets over a network to the central monitoring station. Since the information is encapsulated in packets, the information can be sent over multiple types or combination of network architectures, including a community access television (CATV) network, the public switched telephone network (PSTN), the integrated services digital network (ISDN), the Internet, a local area network (LAN), a wide area network (WAN), over a wireless communications network, or over asynchronous transfer mode (ATM) network. A separate transmission code is not required for each different type of transmission media.

One of the advantages of the Pfeifer invention is that it enables data of various forms to be formatted in a single packet irrespective of the origin or medium of transmission. However, the data transfer system lacks the capability to remotely debug the performance parameters of the medical interface device or the programmer. Further, Pfeifer does not disclose a method or structure by which the medical data in transmission is secured to protect privacy and eliminate data privacy by unauthorized personnel.

In a related art, Thompson discloses a patient tracking system in a co-pending application entitled "World-wide Patient Location and Data Telemetry System For Implantable Medical Devices", Ser. No. 09/045,272, filed on Mar. 20, 1998 which is incorporated by reference herein in its entirety. The disclosure provides additional features for patient tracking in a mobile environment worldwide via the GPS system. However, the concepts advanced by the present invention are not within the purview of the Thompson disclosure because there is no teaching of a web-based environment in which a programmer is in secure data communications with a remote expert data center to exchange patient data as needed.

Yet in another related art, Ferek-Petric discloses a system for communication with a medical device in a co-pending application Ser. No. 09/348,506 which is incorporated by reference herein in its entirety. The disclosure relates to a system that enables remote communications with a medical device, such as a programmer. Particularly, the system enables remote communications to inform device experts about programmer status and problems, The experts will then provide guidance and support to the remotely to service personnel or operators located at the programmer. The system may include a medical device adapted to be implanted into a patient; a server PC communicating with the medical device; the server PC having means for receiving data transmitted across a dispersed data communication pathway, such as the Internet; and a client PC having means for receiving data transmitted across a dispersed communications pathway from the SPC. In certain configurations the server PC may have means for transmitting data across a dispersed data communication pathway (Internet) along a first channel and a second channel; and the client PC may have means for receiving data across a dispersed communication pathway from the server PC along a first channel and a second channel.

One of the significant teachings of Ferek Petric's disclosure, in the context of the present invention, includes the implementation of communication systems, associated with IMDs that are compatible with the Internet. Specifically the disclosure advances the art of remote communications between a medical device, such as a programmer, and experts located at a remote location using the Internet. As indicated hereinabove, the communications scheme is structured to primarily alert remote experts to existing or impending problems with the programming device so that prudent action, such as early maintenance or other remedial steps, may be timely exercised. Further, because of the early warning or advance knowledge of the problem, the remote expert would be well informed to provide remote advice or guidance to service personnel or operators at the programmer.

While Ferek-Petric's invention advances the art in communications systems relating to interacting with a programmer via a communication medium such as the Internet, the system does neither propose nor suggest a secure data transmission system in which a local programmer exchanges patient information from IMDs to a remote expert data center in a manner that protects the data from privacy.

Accordingly it would be advantageous to provide a system in which a programmer could uplink to a remote expert data center to exchange pertinent data securely. Yet another desirable advantage would be to provide a system to implement the use of remote expert systems to manage a programmer on a real-time basis by exchanging private data in a secure manner. A further desirable advantage would be to provide a communications scheme that is compatible with various communications media, to promote a fast uplink of a programmer to remote expert systems and specialized data resources while retaining the privacy of the data in transmission. Yet another desirable advantage would be to provide a high speed communications scheme to enable the transmission of high fidelity sound, video and data to advance and implement efficient and secure remote data management of a clinical/therapy system via a programmer thereby enhancing patient clinical care. As discussed herein below, the present invention provides these and other desirable advantages.

SUMMARY OF THE INVENTION

The present invention generally relates to a communications scheme in which a remote web-based expert data center interacts with a patient having one or more implantable medical devices (IMDs) via an associated external medical device, preferably a programmer, located in close proximity to the IMDs. Some of the most significant advantages of the invention include the use of secure communications media between the remote web-based expert data center and the programmer to remotely exchange clinically significant information without compromising the privacy of the medical data in transmission.

In the context of the present invention, one of the many aspects of the invention includes a real-time access of a programmer to a remote web-based expert data center, via a secure communication network, which includes the Internet. The operative structure of the invention includes the remote web-based expert data center, in which an expert system is maintained, having a bi-directional real-time data, sound and video communications with the programmer via a broad range of secure communication link systems. The programmer is in turn in telemetric communications with the IMDs such that the IMDs may uplink to the programmer or the programmer may down link to the IMDs, as needed using secure data transmission systems.

In a further context of the invention, a programmer is remotely identified monitored, assessed and upgraded as needed by importing expert systems from a remote expert data center via a secure wireless or equivalent communications system. The operational and functional software of the embedded systems in the programmer may be remotely adjusted, upgraded or changed as apparent. Some of the software changes may ultimately be implemented in the IMDs as needed by down linking from the programmer to the IMDs. Further, specific components used in programmer-IMD interface will be identified and documented to comply with medical standards.

Yet another context of the invention includes a communications scheme that provides a secure, highly integrated and efficient method and structure of clinical information management in which various networks such as Community access Television, Local area Network (LAN), a wide area network (WAN) Integrated Services Digital Network (ISDN), the Public Switched telephone Network (PSTN), the Internet, a wireless network, an asynchronous transfer mode (ATM) network, a laser wave network, satellite, mobile and other similar networks are implemented to transfer voice, data and video between the remote data center and a programmer. In the preferred embodiment, wireless communications systems, a modem and laser wave systems are illustrated as examples only and should be viewed without limiting the invention to these types of communications alone. Further, in the interest of simplicity, the applicants refer to the various communications system, in relevant parts, as a communication systems. However, it should be noted that the communication systems, in the context of this invention, are interchangeable and may relate to various schemes of cable, fiber optics, microwave, radio, laser and similar communications or any practical combinations thereof.

Yet one of the other distinguishing features of the invention includes the use a highly flexible and adaptable communications scheme to promote secure continuous and real-time communications between a remote expert data center and a programmer associated with a plurality of IMDs. The IMDs are structured to share information intracorporeally and may interact with the programmer, as a unit. Specifically, the IMDs either jointly or severally can be interrogated to implement or extract clinical information as required. In other words, all of the IMDs may be accessed via one IMD or, in the alternate, each one of the IMDs may be accessed individually. The information collected in this manner may be transferred to the programmer by up linking the IMDs as needed.

Further, the present invention provides significant advantages over the prior art by enabling the acquisition of a secure and automated self-identification information of a programmer remotely. The automated self-identification scheme is compatible with a global preferably web-based data center which is configured to interrogate and obtain the identification of components. Primarily, the component-identification procedure relates to the programmer-IMD sessions. Components used in these sessions are identified and centrally logged for reference and compliance requirements. Generally, the web-based expert data center will interrogate the programmer to identify components used in the sessions.

The invention provides significant compatibility and scalability to other web-based applications such as telemedicine and emerging web-based technologies such as tele-immersion. For example, the system may be adapted to webtop applications in which a webtop unit may be used to uplink the patient to a remote data center for non-critical information exchange between the IMDs and the remote expert data center. In these and other web-based similar applications the data collected, in the manner and substance of the present invention, may be used as a preliminary screen to identify the need for further intervention using advanced web technologies.

Accordingly, the invention provides solutions to certain problems existing in the prior art such as: (a) an inability to securely transmit sensitive data from a programmer to a receiving device across a public network; (b) an inability to authenticate and uniquely identify the source of a data transmission from a medical device; (c) an inability to provide a secure means to transmit operational attributes of a medical device to the manufacturer of the medical device; (d) an inability to provide the manufacturer of a medical device with a secure means for downloading software updates to a programmer; and (e) an inability to provide the manufacturer of a medical device with a secure means to transmit sensitive patient data from a centralized computer to a programmer across a public network.

Further, the system and method of the invention provide certain advantages, including: (a) the ability to provide a secure data exchange between a programmer and a computer across a public network; (b) the ability to uniquely identify the source of a data transmission from a medical device via a digital signature; (c) the ability to validate the authenticity of a communication directed toward a programmer from a computer; (d) the ability to directly exchange sensitive patient data between two programmers across a public network via data encryption; and (e) the ability to securely transmit operational attributes of a medical device to the manufacturer of the medical device.

The system and method of the invention include certain features, including a data encryption engine present within a programmer for encrypting sensitive information obtained by the programmer. The invention also includes a feature to transmit the encrypted patient data from the programmer to a computer via a public communication media network. Another feature of the invention is a data decryption engine present within the computer for decrypting the encrypted patient data created by the programmer. Yet another feature of the invention is a key source which provides the encryption engine and decryption engine with a set of keys utilized by the encryption/decryption process.

Other objects, advantages, and features of the invention will become apparent by referring to the appended drawings, detailed description, and claims.

BRIEF DESCRIPTION OF THE DRAWINGS

The present invention will be appreciated as the same becomes better understood by reference to the following detailed description of the preferred embodiment of the invention when considered in connection with the accompanying drawings, in which like numbered reference numbers designate like parts throughout the figures thereof, and wherein:

FIG. 2 is a block diagram representing the major components of an IMD;

FIG. 3A is a block diagram presenting the major components of a programmer or webtop unit;

FIG. 3B is a block diagram representing a laser transceiver for high speed transmission of voice, video and other data;

DESCRIPTION OF THE PREFERRED EMBODIMENTS

Figure 1:
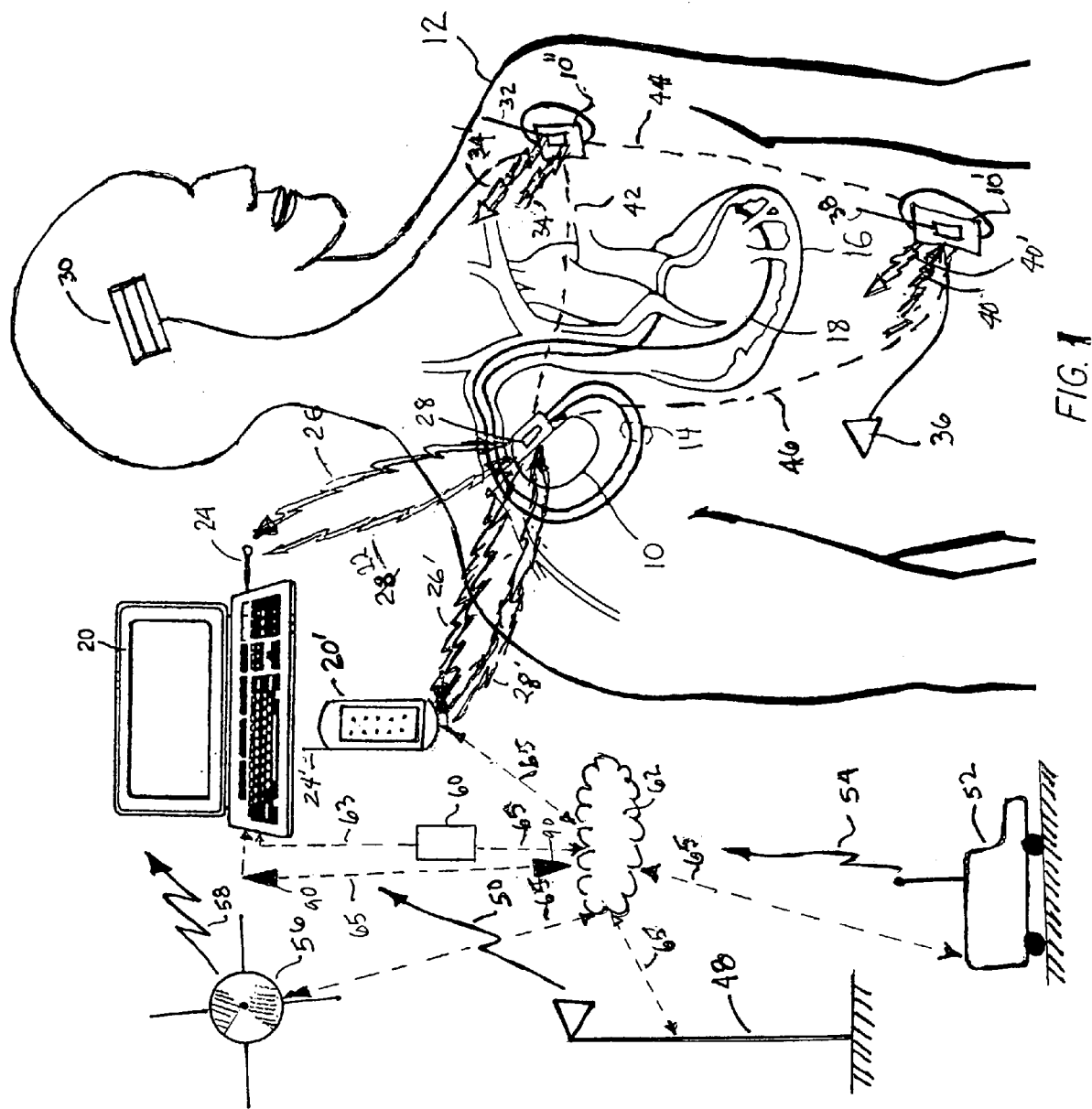
FIG. 1 is a simplified schematic diagram of major uplink and downlink telemetry communications between a remote clinical station, a programmer and a plurality of implantable medical devices (IMDs)

FIG. 1 is a simplified schematic of the major components of the present invention. Specifically, a bi-directional wireless communications system between programmer 20, webtop unit 20' and a number of implantable medical devices (IMDS) represented by IMD 10, IMD 10' and IMD 10" is shown. The IMDs are implanted in patient 12 beneath the skin or muscle. The IMDs are electrically coupled to electrodes 18, 30, and 36 respectively in a manner known in the art. IMD 10 contains a microprocessor for timing, sensing and pacing functions consistent with preset programmed functions. Similarly, IMDs 10' and 10" are microprocessor-based to provide timing and sensing functions to execute the clinical functions for which they are employed. For example, IMD 10' could provide neural stimulation to the brain via electrode 30 and IMD 10" may function as a drug delivery system that is controlled by electrode 36. The various functions of the IMDs are coordinated using wireless telemetry. Wireless links 42, 44 and 46 jointly and severally couple IMDs 10, 10' and 10" such that programmer 20 may transmit commands or data to any or all the of IMDs via one of telemetry antennas 28, 32 and 38. This structure provides a highly flexible and economical wireless communications system between the IMDS. Further, the structure provides a redundant communications system, which enables access to any one of a multiplicity of IMDs in the event of a malfunction of one or two of antennas 28, 32 and 38.

Programming commands or data are transmitted from programmer 20 to IMDs 10, 10' and 10" via external RF telemetry antenna 24. Telemetry antenna 24 may be an RF head or equivalent. Antenna 24 may be located on programmer 20 externally on the case or housing. Telemetry antenna 24 is generally telescoping and may be adjustable on the case of programmer 20. Both programmer 20 and webtop unit 20' may be placed a few feet away from patient 12 and would still be within range to wirelessly communicate with telemetry antennas 28, 32 and 38.

The uplink to remote web-based expert data center 62, hereinafter referred to as, interchangeably, "data center 62", "expert data center 62" or "web-based data center 62" without limitations, is accomplished through programmer 20 or webtop unit 20'. Accordingly programmer 20 and webtop unit 20' function as an interface between IMDs 10, 10' and 10" and data center 62. One of the many distinguishing elements of the present invention includes the use of various scalable, reliable and high-speed wireless communication systems to bi-directionally transmit high fidelity digital/analog data between programmer 20 and data center 62.

There are a variety of wireless mediums through which data communications could be established between programmer 20 or webtop unit 20' and data center 62. The communications link between Programmer 20 or webtop unit 20' and data center 62 could be modem 60, which is connected to programmer 20 on one side at line 63 and data center 62 at line 64 on the other side. In this case, data is transferred from data center 62 to programmer 20 via modem 60. Alternate data transmission systems include, without limitations, stationary microwave and/or RF antennas 48 being wirelessly connected to programmer 20 via tunable frequency wave delineated by line 50. Antenna 48 is in communications with data center 62 via wireless link 65. Similarly, webtop unit 20', mobile vehicle 52 and satellite 56 are in communications with data center 62 via wireless link 65. Further, mobile system 52 and satellite 56 are in wireless communications with programmer 20 or webtop unit 20' via tunable frequency waves 54 and 58, respectively.

In the preferred embodiment a Telnet system is used to wirelessly access data center 62. Telnet emulates a client/server model and requires that the client run a dedicated software to access data center 62. The Telnet scheme envisioned for use with the present invention includes various operating systems including UNIX, Macintosh, and all versions of Windows.

Functionally, an operator at programmer 20 or an operator at data center 62 would initiate remote contact. Programmer 20 is down linkable to IMDs via link antennas 28, 32 and 38 to enable data reception and transmission. For example, an operator or a clinician at data center 62 may downlink to programmer 20 to perform a routine or a scheduled evaluation of programmer 20. In this case the wireless communication is made via wireless link 65. If a downlink is required from programmer 20 to IMD 10 for example, the downlink is effected using telemetry antenna 22. In the alternate, if an uplink is initiated from patient 12 to programmer 20 the uplink is executed via wireless link 26. As discussed herein below, each antenna from the IMDs can be used to uplink all or one of the IMDs to programmer 20. For example, IMD 10" which relates to neural implant 30 can be implemented to up-link, via wireless antenna 34 or wireless antenna 34', any one, two or more IMDs to programmer 20. Preferably bluetooth chips, adopted to function within the body to outside the body and also adopted to provide low current drain, are embedded in order to provide wireless and seamless connections 42, 44 and 46 between IMDs 10, 10' and 10". The communication scheme is designed to be broadband compatible and capable of simultaneously supporting multiple information sets and architecture, transmitting at relatively high speed, to provide data, sound and video services on demand.

FIG. 2 illustrates typical components of an IMD, such as those contemplated by the present invention. Specifically, major operative structures common to all IMDs 10, 10' and 10" are represented in a generic format. In the interest of brevity, IMD 10 relative to FIG. 2 refers to all the other IMDs. Accordingly, IMD 10 is implanted in patient 12 beneath the patient's skin or muscle and is electrically coupled to heart 16 of patient 12 through pace/sense electrodes and lead conductor(s) of at least one cardiac pacing lead 18 in a manner known in the art. IMD 10 contains timing control 72 including operating system that may employ microprocessor 74 or a digital state machine for timing, sensing and pacing functions in accordance with a programmed operating mode. IMD 10 also contains sense amplifiers for detecting cardiac signals, patient activity sensors or other physiologic sensors for sensing the need for cardiac output, and pulse generating output circuits for delivering pacing pulses to at least one heart chamber of heart 16 under control of the operating system in a manner well known in the prior art. The operating system includes memory registers or RAM/ROM 76 for storing a variety of programmed-in operating mode and parameter values that are used by the operating system. The memory registers or RAM/ROM 76 may also be used for storing data compiled from sensed cardiac activity and/or relating to device operating history or sensed physiologic parameters for telemetry out on receipt of a retrieval or interrogation instruction. All of these functions and operations are well known in the art, and many are generally employed to store operating commands and data for controlling device operation and for later retrieval to diagnose device function or patient condition.

Programming commands or data are transmitted between IMD 10 RF telemetry antenna 28, for example, and an external RF telemetry antenna 24 associated with programmer 20. In this case, it is not necessary that the external RF telemetry antenna 24 be contained in a programmer RF head so that it can be located close to the patient's skin overlying IMD10. Instead, the external RF telemetry antenna 24 can be located on the case of programmer 20. It should be noted that programmer 20 can be located some distance away from patient 12 and is locally placed proximate to the IMDs such that the communication between IMDs 10, 10' and 10" and programmer 20 is telemetric. For example, programmer 20 and external RF telemetry antenna 24 may be on a stand a few meters or so away from patient 12. Moreover, patient 12 may be active and could be exercising on a treadmill or the like during an uplink telemetry interrogation of real time ECG or other physiologic parameters. Programmer 20 may also be designed to universally program existing IMDs that employ RF telemetry antennas of the prior art and therefore also have a conventional programmer RF head and associated software for selective use therewith.

In an uplink communication between IMD 10 and programmer 20, for example, telemetry transmission 22 is activated to operate as a transmitter and external RF telemetry antenna 24 operates as a telemetry receiver. In this manner data and information may be transmitted from IMD 10 to programmer 20. In the alternate, IMD 10 RF telemetry antenna 26 operates as a telemetry receiver antenna to downlink data and information from programmer 20. Both RF telemetry antennas 22 and 26 are coupled to a transceiver comprising a transmitter and a receiver.

FIG. 3A is a simplified circuit block diagram of major functional components of programmer 20. The external RF telemetry antenna 24 on programmer 20 is coupled to a telemetry transceiver 86 and antenna driver circuit board including a telemetry transmitter and telemetry receiver 34. The telemetry transmitter and telemetry receiver are coupled to control circuitry and registers operated under the control of microcomputer 80. Similarly, within IMD 10, for example, the RF telemetry antenna 26 is coupled to a telemetry transceiver comprising a telemetry transmitter and telemetry receiver. The telemetry transmitter and telemetry receiver in IMD 10 are coupled to control circuitry and registers operated under the control of microcomputer 74.

Further referring to FIG. 3A, programmer 20 is a personal computer type, microprocessor-based device incorporating a central processing unit, which may be, for example, an Intel Pentium microprocessor or the like. A system bus interconnects CPU 80 with a hard disk drive, storing operational programs and data, and with a graphics circuit and an interface controller module. A floppy disk drive or a CD ROM drive is also coupled to the bus and is accessible via a disk insertion slot within the housing of programmer 20. Programmer 20 further comprises an interface module, which includes a digital circuit, a non-isolated analog circuit, and an isolated analog circuit. The digital circuit enables the interface module to communicate with interface controller module. Operation of the programmer in accordance with the present invention is controlled by microprocessor 80.

In order for the physician or other caregiver or operator to communicate with the programmer 20, a keyboard or input 82 coupled to CPU 80 is optionally provided. However the primary communications mode may be through graphics display screen of the well-known "touch sensitive" type controlled by a graphics circuit. A user of programmer 20 may interact therewith through the use of a stylus, also coupled to a graphics circuit, which is used to point to various locations on screen or display 84 which display menu choices for selection by the user or an alphanumeric keyboard for entering text or numbers and other symbols. Various touch-screen assemblies are known and commercially available. Display 84 and or the keyboard comprise means for entering command signals from the operator to initiate transmissions of downlink or uplink telemetry and to initiate and control telemetry sessions once a telemetry link with data center 62 or an implanted device has been established. Display screen 84 is also used to display patient related data and menu choices and data entry fields used in entering the data in accordance with the present invention as described below. Display screen 84 also displays a variety of screens of telemetered out data or real time data. Display screen 84 may also display plinked event signals as they are received and thereby serve as a means for enabling the operator to timely review link-history and status.

Programmer 20 further comprises an interface module, which includes digital circuit, non-isolated analog circuit, and isolated analog circuit. The digital circuit enables the interface module to communicate with the interface controller module. As indicated hereinabove, the operation of programmer 20, in accordance with the present invention, is controlled by microprocessor 80. Programmer 20 is preferably of the type that is disclosed in U.S. Pat. No. 5,345,362 to Winkler, which is incorporated by reference herein in its entirety.

Screen 84 may also display up-linked event signals when received and thereby serve as a means for enabling the operator of programmer 20 to correlate the receipt of uplink telemetry from an implanted device with the application of a response-provoking action to the patient's body as needed.

Programmer 20 is also provided with a strip chart printer or the like coupled to interface controller module so that a hard copy of a patient's ECG, EGM, marker channel of graphics displayed on the display screen can be generated.

As will be appreciated by those of ordinary skill in the art, it is often desirable to provide a means for programmer 20 to adapt its mode of operation depending upon the type or generation of implanted medical device to be programmed and to be compliant with the wireless communications system through which data and information is transmitted between programmer 20 and data center 62.

FIG. 3B is an illustration of the major components of Wave unit 90 utilizing laser technologies such as for example the WaveStar Optic Air Unit, manufactured by Lucent Technologies or equivalent. This embodiment may be implemented for large data transfer at high speed in applications involving several programmers. The unit includes laser 92, transceiver 94 and amplifier 96. A first wave unit 90 is installed at data center 62 and a second unit 90' is located proximate to programmer 20 or webtop unit 20'. Data transmission between remote data center 62 and programmer unit 20 is executed via wave units 90. Typically, the first wave unit 90 accepts data and splits it into unique wavelength for transmission. The second wave unit 90' recomposes the data back to its original form.

Figure 4:
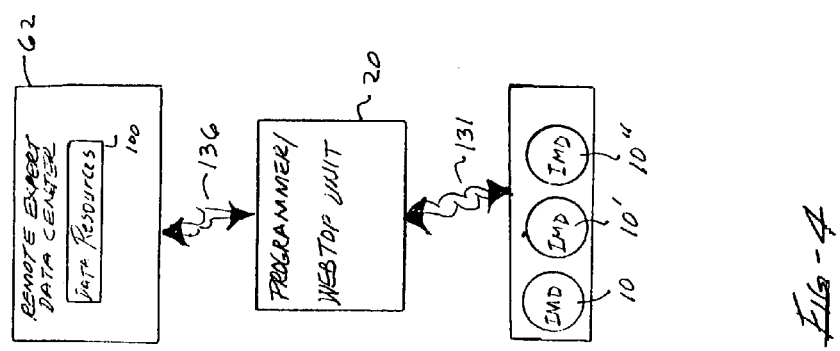
FIG. 4 is a block diagram illustrating the organizational structure of the wireless communication system in accordance with the present invention.

FIG. 4 is a simplified block diagram illustrating the principal systems of the invention. The Remote expert system or data center 62 includes data resource 100. As discussed hereinabove, data center 62 is preferably in wireless communications with programmer 20. The medium of communications between programmer 20 and data center 62 may be selected from one or a combination of several cable and wireless systems discussed hereinabove. Further, programmer 20 is in wireless communications with a number of IMDs, such as shown in FIG. 1. Although three IMDs are shown for illustrative purposes, it should be noted that several IMDs may be implemented and the practice of the present invention does not limit the number of implants per se.

Figure 5:
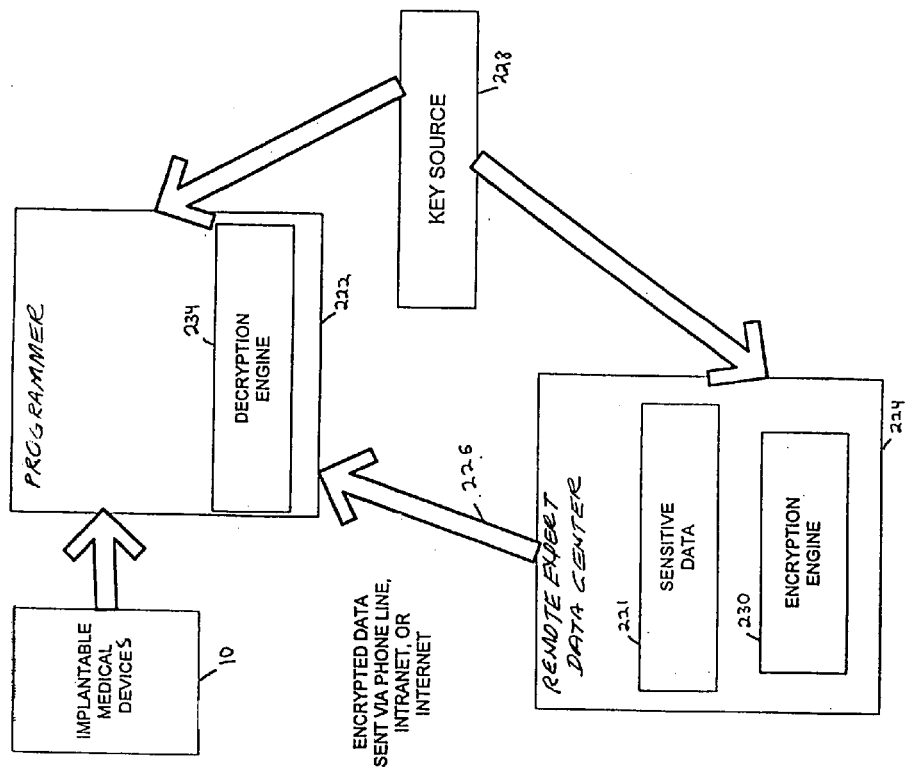
FIG. 5 is a block diagram illustrating a first embodiment of a secure data transfer mechanism in accordance with the present invention.

FIG. 5 is a block diagram illustrating one embodiment of a secure data transfer structural scheme in accordance with the present invention, shown generally at 220. In this embodiment, sensitive information 221 (such as patient information) is transferred in encrypted form from programmer 222 to remote expert data center/remote data center across data communications media/connection 226. Data communication media 226 is an interface for intercoupling programmer 222 and remote data center 224. Data communication media 226 could be configured to include a telephone line connection, an intranet connection, an internet connection, a satellite connection, a laser system, a constellation of satellite connections, a global positioning system (GPS) connection, or any combination thereof.

Key source 228 provides both programmer 222 and remote data center 224 with encryption/decryption keys for encrypting/decrypting sensitive information 221. In one embodiment of the invention, key source 228 distributes symmetric encryption/decryption keys. In another embodiment of the invention, key source 228 distributes asymmetric keys (i.e., pubic/private keys). If the encryption/decryption algorithms employed by the invention are standard algorithms known to the public, additional security measures must be taken in the disbursement of the keys from key source 228 to programmer 222 and 224 in order to ensure privacy. In addition to sensitive patient information, the invention may also securely transfer other forms of sensitive information 221, including: physician data, customer data, and/or manufacturer data to remote export data center 224.

Programmer 222 is any instrument capable of obtaining, storing, and transmitting sensitive information 221. Programmer 222 is capable of being coupled to IMDs 10m 10'; 10". IMD 10 obtains sensitive information 221 from the patient, then transfers the sensitive patient information to programmer 222.

Before sensitive information 221 is transmitted across data communication media 226, sensitive information 221 is encrypted by encryption engine 230. Encryption engine 230 encrypts sensitive information 221 by use of an encryption algorithm and a key. In essence, encryption engine 230 converts sensitive information 221 to a random scrambled message. Encryption engine 230 produces different encrypted scrambled messages depending on the specific value and format of the encryption key. Various encryption algorithms may be utilized within the framework and context of the invention. In one embodiment, the invention utilizes a symmetric key cryptography type algorithm (i.e., the same key is used by programmer 222 and remote data center 224 to encrypt and decrypt sensitive information 221). Examples of symmetric key cryptography types include Data Encryption Standard (DES) and International Data Encryption Algorithm (IDEA). In another preferred embodiment, the invention utilizes a public key/private key cryptography encryption type algorithm (i.e., different keys are used by programmer 222 and remote data center 224 to encrypt and decrypt sensitive information 221). Examples of public key cryptography encryption types include the Rivest, Shamie and Adleman algorithm (RSA) and Pretty Good Privacy (PGP).

In one embodiment of the invention, encryption engine 230 also adds a digital signature to sensitive information 221 transmitted by programmer 222. As stated earlier, digital signatures are useful in validating the authenticity of a communication. A digital signature can be used in conjunction with a message containing sensitive information 221 by first creating a message digest (a 128 bit hashed representation of a message) with the sender's (e.g., programmer 222) private key, attaching the message digest to the message, then encrypting both the message digest and the message with the recipient's (e.g., remote data center 224) public key. The recipient reverses these steps, first decrypting the message with the recipient's private key, then decrypting the signature with the sender's public key.

After sensitive information 221 has been encrypted, the encrypted sensitive information is transmitted to remote data center 224 via data communications media 226. In alternate embodiments, data communication media 226 is implemented via a telephone line connection, an intranet connection, an internet connection, a satellite connection, a constellation of satellite connections, a global positioning system (GPS) connection, or any combination thereof. Data communication media 226 may be exposed to security vulnerabilities, for example, during the transmittal of sensitive information 221 from programmer 222 to remote data center 224. By encrypting sensitive information 221 before transmission, the confidentiality of the information is preserved.

Remote data center 224 receives the encrypted sensitive information 221 transmitted by programmer 222. In one embodiment of the invention, remote data center 224 is a second remote medical instrument 221. Decryption engine 234 resides on remote data center 224, and decrypts the encrypted sensitive information using a decryption algorithm corresponding to the encryption algorithm and a decryption key corresponding to the encryption key that was used to originally encrypt the message. The output of decryption engine 234 is the original, unencrypted sensitive information 221.

Figure 6:
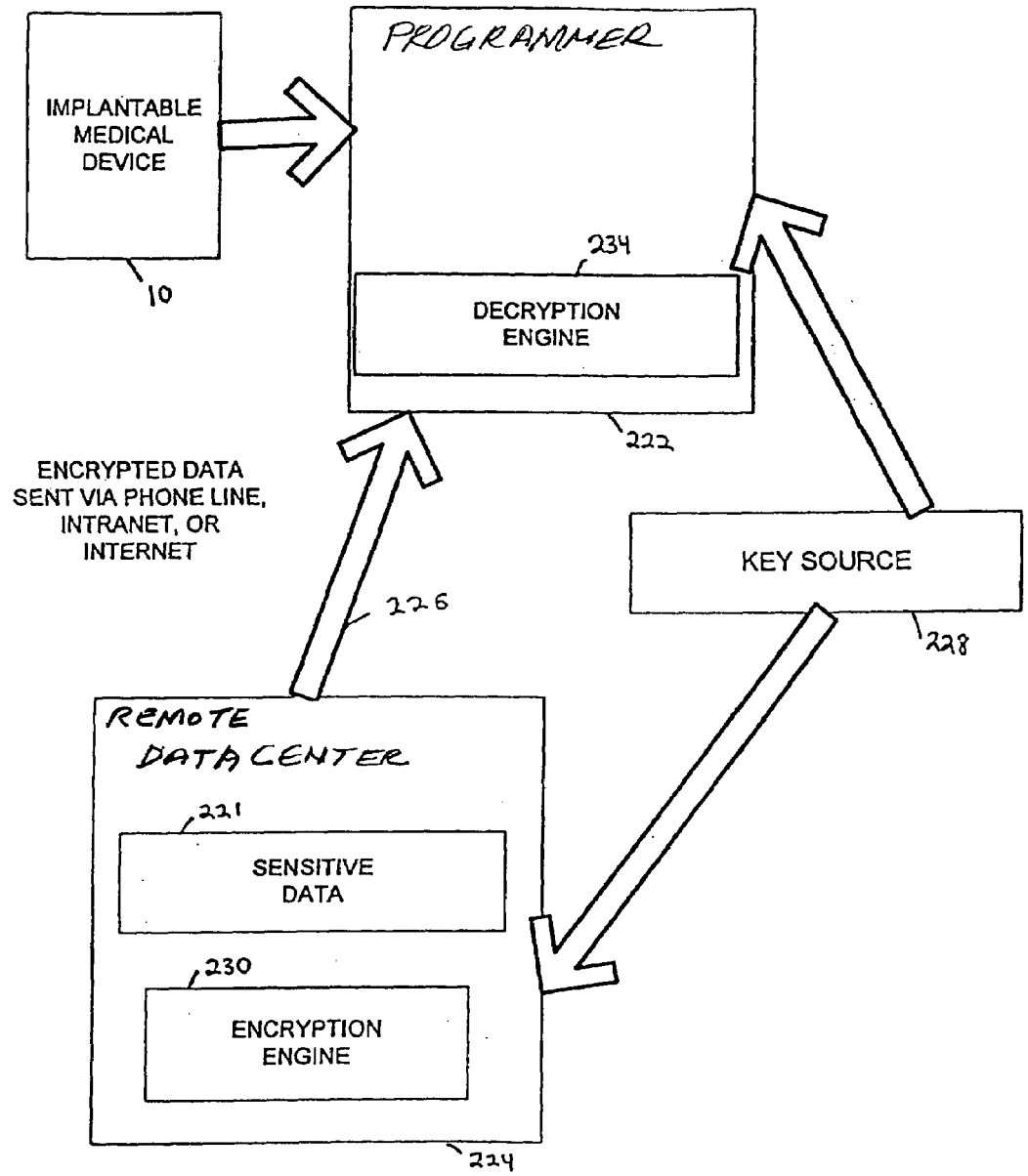
FIG. 6 is a block diagram illustrating a second embodiment of a secure data transfer mechanism in accordance with the present invention.

FIG. 6 is a block diagram illustrating another embodiment of a secure data transfer structural scheme in accordance with the present invention. In sharp contrast to the embodiment of the secure data transfer mechanism previously illustrated in FIG. 5, the embodiment illustrated in FIG. 6 transfers encrypted sensitive information 221 from remote data center 224 to remote instrument 222.

In this embodiment, sensitive information 221 resides on remote data center 224. Remote data center 224 includes an encryption engine 230 for encrypting sensitive information 221 prior to transfer to programmer 222 via data communications media/connection 226. In alternate embodiments, data communication media 226 is implemented via a telephone line connection, an intranet connection, an internet connection, a satellite connection, a constellation of satellite connections, a global positioning system (GPS) connection, or any combination thereof. Programmer 222 includes decryption engine 226 for decrypting encrypted sensitive information 221 after encrypted sensitive information 221 has been transferred by remote data center 224. Key source 228 provides both programmer 222 and remote data center 224 with encryption/decryption keys for encrypting/decrypting sensitive information 221.

This embodiment of the invention shown in FIG. 6 is useful when sensitive information 221, such as patient data, manufacturer data, or operational data, needs to be securely transferred from remote data center 224 to programmer 222. For example, a patient monitored by a first programmer moves to a different part of the country, and switches health care providers. Sensitive information 221 from the patient can first be transferred from the first programmer to remote data center 224, as previously illustrated in FIG. 5. Then, sensitive information 221 can be transferred from remote data center 224 to a second programmer at the new health care provider, as illustrated in FIG. 6. Accordingly, sensitive information 221 can be quickly and securely transferred between two or more programmers 222, via remote data center 224.

In another application of the invention, the manufacturer of programmer 222 may wish to update software applications or other manufacturer specific information on programmer 222. Since manufacturer specific information may include sensitive, proprietary information such as software updates or new software modules, it is imperative to the manufacturer that this sensitive, proprietary information be carefully protected. Rather than manually installing the manufacturer updates at a programmer location (which may be time consuming depending on the location of the programmer), the invention enables the secure transfer of manufacturer updates using the various encryption techniques or equivalent structure and methods disclosed herein.

Figure 7:
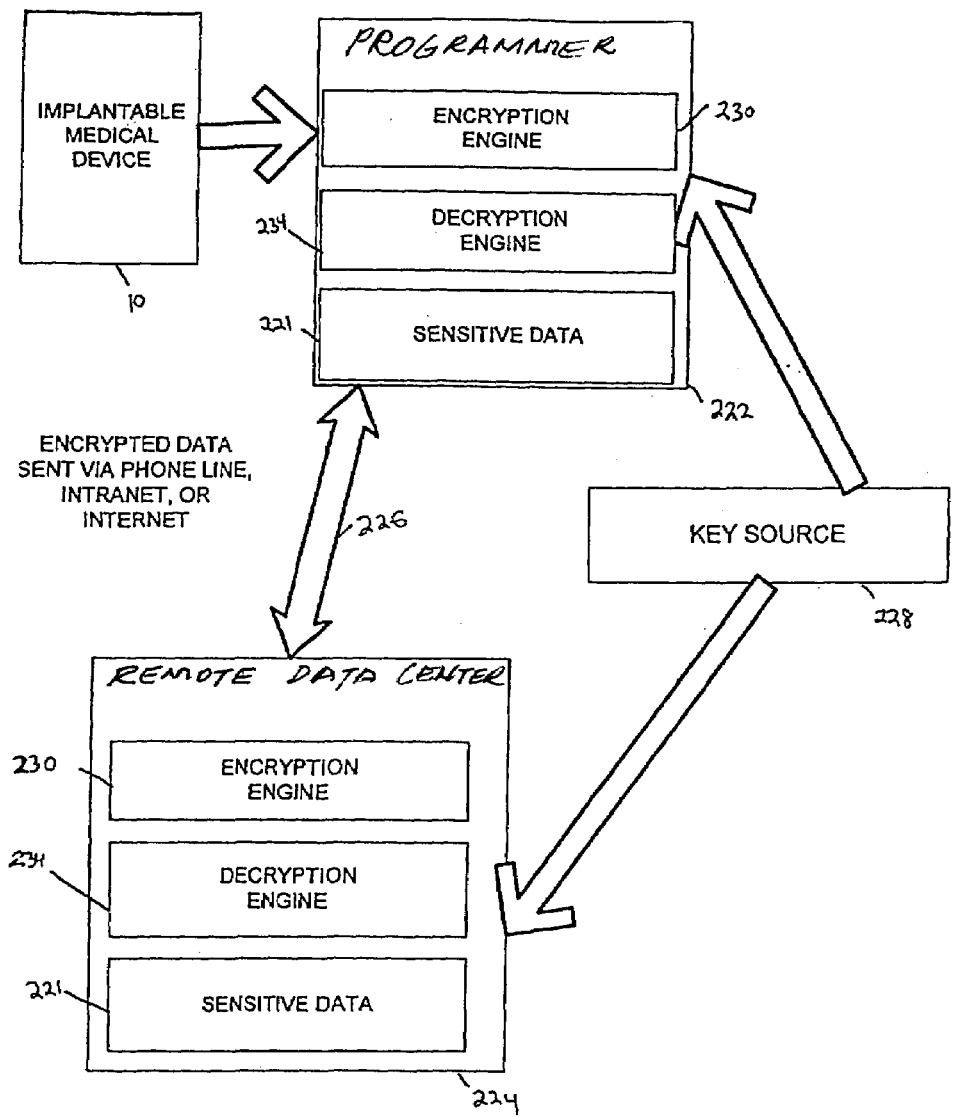
FIG. 7 is a block diagram illustrating a third embodiment of a secure data transfer mechanism in accordance with the present invention.

FIG. 7 is a block diagram illustrating yet another embodiment of a secure data transfer structure and method in accordance with the invention. In contrast to the unidirectional data transfer capabilities previously illustrated (i.e., data transfer from programmer 222 to remote data center 224 and data transfer from remote data center 224 to programmer 222), this embodiment allows bi-directional data transmission of encrypted sensitive information between remote data center 224 and programmer 222.

In the embodiment shown in FIG. 7, programmer 222 contains both encryption engine 230 and decryption engine 234. Similarly, remote data center 224 contains both encryption engine 230 and decryption engine 234. Key source 228 provides both programmer 222 and remote data center 224 with encryption/decryption keys for encrypting/decrypting sensitive information 221 residing on programmer 222 and/or remote data center 224. Sensitive data is transferred between programmer 222 and remote data center 224 via data communication media 226. In alternate embodiments, data communication media 226 is implemented via a telephone line connection, an intranet connection, an internet connection, a satellite connection, a constellation of satellite connections, a global positioning system (GPS) connection, or any combination thereof.

In one application of the embodiment shown in FIG. 7, direct transfer of encrypted sensitive information 221 can occur directly between two or more programmers 222. In other words, remote data center 224 can be a second programmer. Since, in this example, each programmer 222 supports bi-directional secure data transfer (i.e., includes both an encryption engine and a decryption engine), a separate remote data center 224 is no longer needed to support communications between two or more programmers 222, as illustrated previously in FIG. 6.

Figure 8:
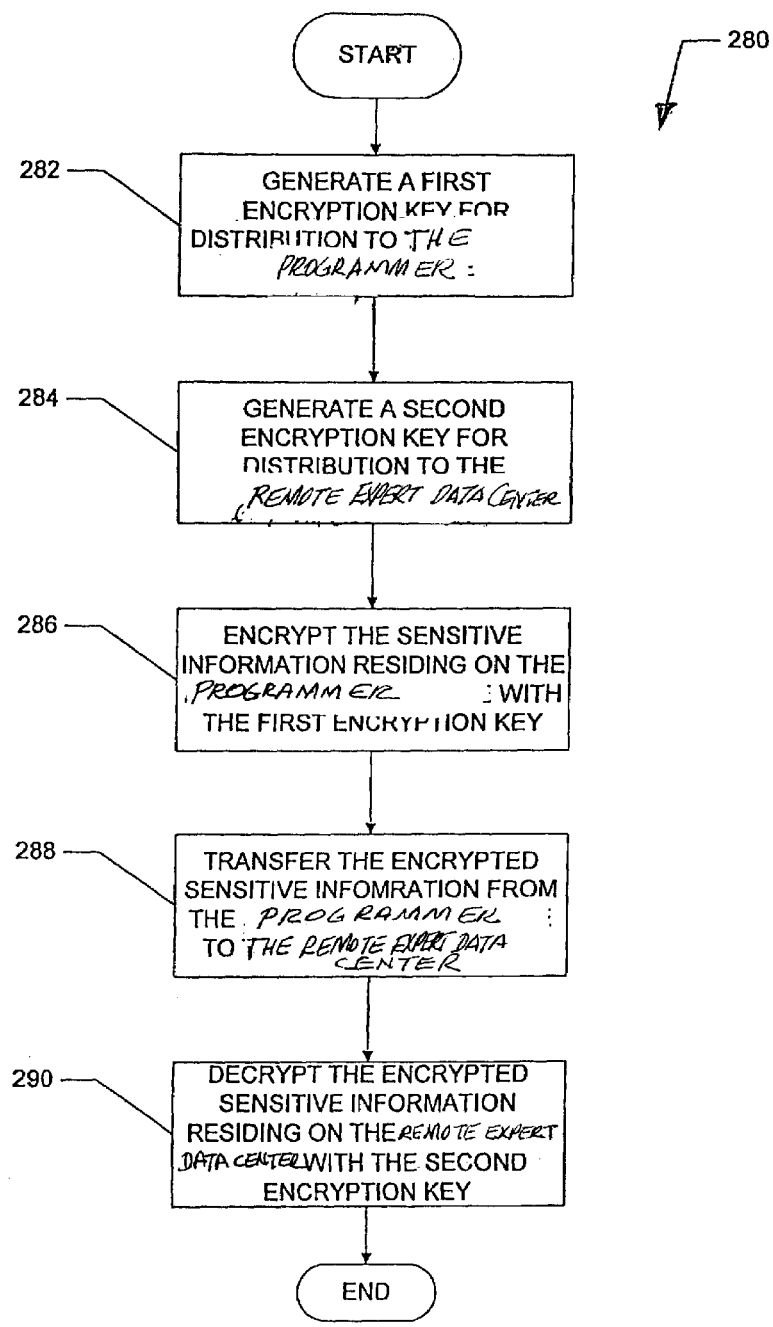
FIG. 8 is a flow chart illustrating a method for securely transmitting sensitive information from a programmer to a computer in accordance with the present invention.

FIG. 8 is a flow chart illustrating a method for securely transmitting sensitive patient information from programmer 222 to remote data center 224 in-accordance with the invention, as shown generally at 280. The method begins by generating a first encryption key for distribution to programmer 222, as shown at step 282. At step 284, a second encryption key is generated for distribution to remote data center 224. Both the first encryption key and the second encryption key are generated by key source 228, shown in FIGS. 5–7. A number of different previously discussed algorithms may be used to generate the first encryption key and the second encryption key. In one embodiment of the invention, the first encryption key and the second encryption key are the same (i.e., symmetric key encryption). In another embodiment of the invention, the first encryption key and the second encryption key are different (i.e., public/private key encryption). In both embodiments, the first encryption key and the second encryption key are related so that an encrypted file produced by the first encryption key may be decrypted by the second encryption key.

At step 286, sensitive information (such as sensitive information 221) residing on programmer 222 is encrypted with the first encryption key. An encryption algorithm resident on programmer 222 takes sensitive information 221 and the first encryption key as inputs and produces a file containing the encrypted sensitive information as an output.

Next, encrypted sensitive information 221 is transferred from programmer 222 to the remote data center 224 via data communication media/connection 226, as shown in step 288. In alternate embodiments, data communication media/connection 226 is accomplished via a telephone line connection, an intranet connection, an internet connection, a satellite connection, a constellation of satellite connections, a global positioning system (GPS) connection, or any combination thereof. As stated earlier, data communication media/connection 226 may experience security vulnerabilities which compromise the security of sensitive information 221 as the information is transmitted from programmer 222 to remote data center 224. By encrypting sensitive information 221 before transmission, the confidentiality of the information is preserved during transmission on data communication media/connection 226.

Finally, encrypted sensitive information 221 now residing on remote data center 224 is decrypted with the second encryption key, as shown at step 290. Decryption engine 234 takes encrypted sensitive information 221 and the second encryption key as input, and generates the original, unencrypted sensitive information 221 for use by remote data center 224.

Figure 9:
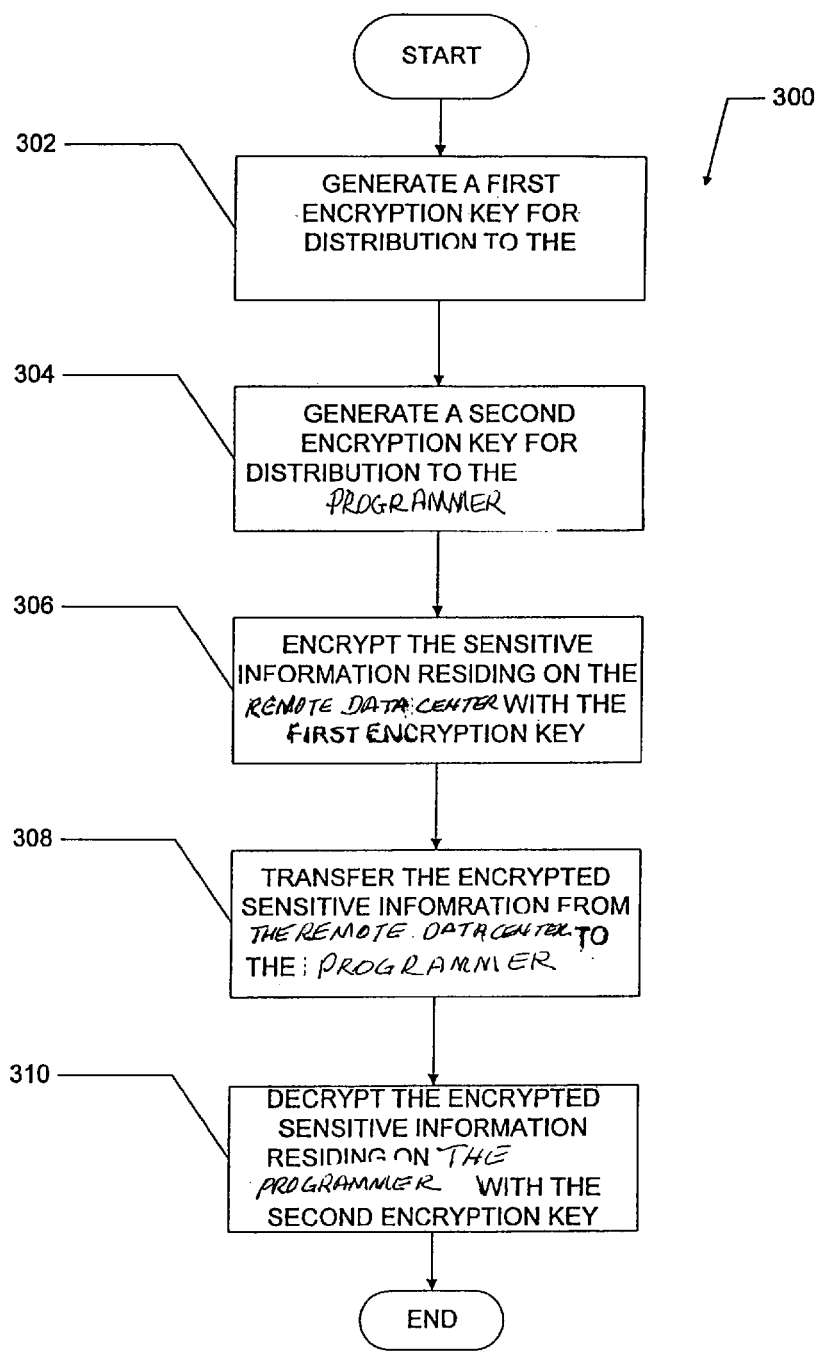
FIG. 9 is a flow chart illustrating a method for securely transmitting sensitive information from a computer to a programmer in accordance with the present invention.

FIG. 9 is another flow chart illustrating a method for securely transmitting sensitive information 221 from remote data center 224 to programmer 222 in accordance with the invention, as shown generally at 300. In sharp contrast to the method illustrated in FIG. 8, the method of FIG. 9 describes the transfer of sensitive information 221 from remote data center 224 to programmer 222.

The method begins by generating a first encryption key for distribution to the computer, as shown at step 302. Next, a second encryption key is generated for distribution to programmer 222, as shown at step 304. Both the first encryption key and the second encryption key are generated by key source 228 shown in FIGS. 6–8. A number of different algorithms, some of which are described above, may be used to generate the first encryption key and the second encryption key. In one embodiment, the first encryption key and the second encryption key are the same (i.e., symmetric key encryption). In another embodiment, the first encryption key and the second encryption key are different (i.e., public/private key encryption). In both embodiments, the first encryption key and the second encryption key are related so that an encrypted file produced by the first encryption key may be decrypted by the second encryption key.

At step 306, sensitive information 221 residing on remote data center 224 is encrypted with the first encryption key. An encryption algorithm resident on remote data center 224 takes sensitive information 221 and the first encryption key as input, then produces an output file containing encrypted sensitive information 221.

Encrypted sensitive information 221 is then transferred from remote data center 224 to programmer 222, as shown at step 308. Finally, encrypted sensitive information 221 now residing on programmer 222 is decrypted with the second encryption key, as shown at step 310. Decryption engine 234 takes encrypted sensitive information 221 and the second encryption key as inputs, and generates the original, unencrypted sensitive information 221 for use at programmer 222.

Figure 10:
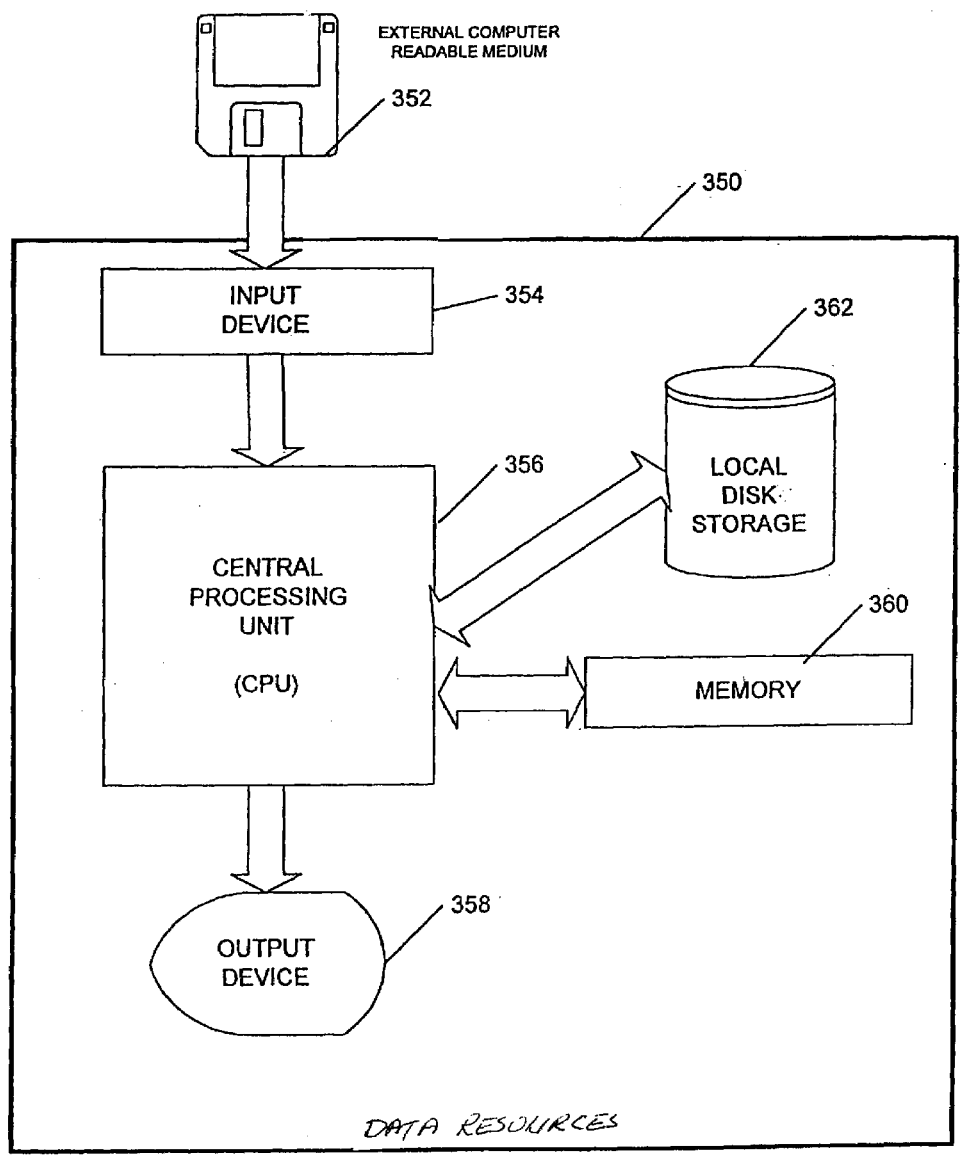
FIG. 10 is a block diagram of a remote data center or a computer system and a corresponding computer readable medium incorporating a method for securely transmitting sensitive patient information from a programmer to a computer in accordance with the present invention.

FIG. 10 is a block diagram of remote data center illustrating elements of data resources 350 and corresponding computer readable medium 352 incorporating a method for securely transmitting sensitive information 221 from programmer 222 to remote data center 224 in accordance with the invention. Embodiments of external computer readable medium 352 include, but not limited to, a CD-ROM, a floppy disk, or a disk cartridge. A secure data transfer method of the invention can be implemented in a variety of compiled and interpreted computer languages. External computer readable medium 352 stores source code, object code, executable code, shell scripts, and/or dynamic link libraries for the secure data transfer method. Input device 354 reads external computer readable medium 352 and provides this data to data recources 350. Embodiments of input device 354 include, but not limited to, a CD-ROM reader, a floppy disk drive, or a data cartridge reader.

System 350 includes central processing unit 356 for executing the secure data transfer method according to the invention. Data resources 350 also includes local disk storage 362 for locally storing the secure data before, during, and after execution. The secure data transfer method also utilizes memory 360 within data resources 350 during execution. Upon execution of the secure data transfer method, output data is produced and directed to output device 358. Embodiments of output device 358 include, but not limited to, a computer display device, a printer, and/or a disk storage device.

Accordingly, the invention provides a system and method for securely transferring sensitive information, such as patient data, from a programmer to a centralized computer or data center via data encryption. The secure data transfer system and method of the present invention protects private patient data from risks that may be encountered while transmitting data across public networks. By implementing specialized data encryption schemes, methods and structures, the present invention enables a remote expert data center to exchange clinical and other patient-related private information over various communications media.

Although specific embodiments of the invention have been set forth herein in some detail, it is understood that this has been done for the purposes of illustration only and is not to be taken as a limitation on the scope of the invention as defined in the appended claims. It is to be understood that various alterations, substitutions, and modifications may be made to the embodiment described herein without departing from the spirit and scope of the appended claims.

What is claimed is:

1. A bi-directional communications system integrated with a remote web-based expert data center wherein a medical programmer for an IMD is uplinked to the web-based expert data center via the bi-directional communications system, the web-based expert data center in configuration with the programmer forming a secure medical information exchange network wherein patient records are transferred, the medical information exchange network comprising:
   a database residing within the programmer for storing sensitive information;
   a key source in data communications with the programmer and the web-based expert data center for transmitting an encryption key to the programmer and a decryption key to the expert-data center;
   an encryption engine residing within the programmer for encrypting the sensitive information using the encryption key;
   an interface for coupling the programmer to the expert data center; and
   a decryption engine residing within the expert data center for decrypting the encrypted sensitive information using the decryption key.

2. The system of claim 1 wherein the programmer device is in telemetric communication with the implantable medical device.

3. The system of claim 2, wherein the sensitive information stored within the database includes data obtained from the implantable medical device.

4. The system of claim 1, wherein the sensitive information stored within the database includes confidential patient information.

5. The system of claim 1, wherein the interface is a telephone line connection.

6. The system of claim 1, wherein the interface is an intranet connection.

7. The system of claim 1, wherein the interface is an internet connection.

8. The system of claim 1, wherein the interface is a satellite connection.

9. The system of claim 1, wherein the interface is a global positioning system connection.

10. The system of claim 1, wherein the interface comprises at least two communication links selected from the group of communication links consisting of a telephone line communication, an intranet communication, an internet communication, a satellite communication, and a global positioning system communication.

11. The system of claim 1, wherein the encryption key and the decryption key are symmetric keys.

12. The system of claim 1, wherein the encryption key and the decryption key are asymmetric keys.

13. The system of claim 1, wherein the encrypted sensitive information includes a digital signature.

14. The system of claim 1, wherein the remote expert data center is a second medical device.

15. A bi-directional communications system integrated with a remote web-based expert data center wherein a medical programmer for an IMD is uplinked to the web-based expert data center via the bi-directional communications system, the web-based expert data center in configuration with the programmer forming a secure medical information exchange network wherein patient records are transferred, the medical information exchange network comprising a system for transferring information from a to a programmer, the system comprising:
   a database residing within the remote expert data center for storing sensitive information;
   a key source in data communications with the programmer and the remote expert data center for distributing an encryption key to the remote expert data center and a decryption key to the programmer;
   an encryption engine residing within the remote expert data center for encrypting the sensitive information using the encryption key;
   an interface for coupling the remote expert data center to the programmer; and
   a decryption engine residing within the programmer for decrypting the encrypted sensitive information using the decryption key.

16. The system of claim 15, wherein the programmer is in telemetric communications with an implantable medical device in a patient.

17. The system of claim 16, wherein the sensitive information stored within the database includes data obtained from the implantable medical device.

18. The system of claim 15, wherein the sensitive information stored within the database includes confidential patient information.

19. The system of claim 15, wherein the interface is a telephone line connection.

20. The system of claim 15, wherein the interface is an intranet connection.

21. The system of claim 15, wherein the interface is an internet connection.

22. The system of claim 15, wherein the interface is a satellite connection.

23. The system of claim 15, wherein the interface is a global positioning system connection.

24. The system of claim 15, wherein the interface consists at least one communication link selected from the group of communication links consisting of a telephone line communication, an intranet communication, an internet communication, a satellite communication, and a global positioning system communication.

25. The system of claim 15, wherein the encryption key and the decryption key are symmetric keys.

26. The system of claim 15, wherein the encryption key and the decryption key are asymmetric keys.

27. The system of claim 15, wherein the encrypted sensitive information includes a digital signature.

28. A system for transferring information between a programmer and a remote expert data center, the system comprising:
- a key source in data communications with the programmer and the remote expert data center for distributing a set of encryption keys to the programmer and the remote expert data center;
- an interface for coupling the programmer to the remote expert data center;
- a first encryption engine residing within the programmer for encrypting a first set of sensitive information residing in the programmer using one of the set of encryption keys generated by the key source;
- a second encryption engine residing within the remote expert data center for encrypting a second set of sensitive information residing in the remote expert data center using one of the set of encryption keys generated by the key source;
- a first decryption engine residing within the programmer for decrypting the second set of sensitive information generated by the second encryption engine; and
- a second decryption engine residing within the remote expert data center for decrypting the first set of sensitive information generated by the first encryption engine.

29. The system of claim 28, wherein the programmer is in electrical communication with an implantable medical device in a patient.

30. The system of claim 29, wherein the first set of sensitive information includes data obtained from the implantable medical device.

31. The system of claim 28, wherein the first set of sensitive information includes confidential patient information.

32. The system of claim 28, wherein the interface is a telephone line connection.

33. The system of claim 28, wherein the interface is an intranet connection.

34. The system of claim 28, wherein the interface is an internet connection.

35. The system of claim 28, wherein the interface is a satellite connection.

36. The system of claim 28, wherein the interface is a global positioning system connection.

37. The system of claim 28, wherein the interface comprises at least one communication link selected from the group of communication links consisting of a telephone line communication, an intranet communication, an internet communication, a satellite communication, and a global positioning system communication.

38. The system of claim 28, wherein the set of encryption keys are symmetric keys.

39. The system of claim 28, wherein the set of encryption keys are asymmetric keys.

40. The system of claim 28, wherein the first set of sensitive information includes a digital signature.

41. The system of claim 28, wherein the second set of sensitive information includes a digital signature.

42. A system for securely transferring sensitive information received from at least one lead positioned within a passageway of a heart related to an implantable medical device to a remote expert data center, the system comprising:
- a programmer in data communication with the implantable medical device for receiving and processing the sensitive information from the implantable medical device;
- a key source in data communication with the programmer and the remote expert data center for distributing an encryption key to the programmer and a decryption key to the remote expert data center;
- an encryption engine residing within the programmer for encrypting the sensitive information using the encryption key;
- an interface for coupling the programmer to a remote expert data center; and
- a decryption engine residing within the remote expert data center for decrypting the encrypted sensitive information using the decryption key.

43. The system of claim 42, wherein the interface is a telephone line connection.

44. The system of claim 42, wherein the interface is an intranet connection.

45. The system of claim 42, wherein the interface is an internet connection.

46. The system of claim 42, wherein the interface is a satellite connection.

47. The system of claim 42, wherein the interface is a global positioning system connection.

48. The system of claim 42, wherein the interface consists of at least one communication link selected from the group of communication links consisting of a telephone line communication, an intranet communication, an internet communication, a satellite communication, and a global positioning system communication.

49. The system of claim 42, wherein the encryption key and the decryption key are symmetric keys.

50. The system of claim 42, wherein the encryption key and the decryption key are asymmetric keys.

51. The system of claim 42, wherein the encrypted sensitive information includes a digital signature.

52. A method of securely transferring sensitive information from a programmer to a remote expert data center, the method comprising:
- generating an encryption key for distribution to the programmer;
- generating a decryption key for distribution to the remote expert data center;
- encrypting the sensitive information residing on the programmer with the encryption key;
- transferring the encrypted sensitive information from the programmer to the remote expert data center; and
- decrypting the encrypted sensitive information residing on the remote expert data center with the decryption key.

53. The method of claim 52, wherein the programmer is connected to an implantable medical device in a patient.

54. The method of claim 52, wherein the step of encrypting the sensitive information residing on the programmer further comprises:
- creating a digital signature for the encrypted sensitive information.

55. The method of claim 54, wherein the step of decrypting the encrypted sensitive information residing on the remote expert data center further comprises:
- verifying the digital signature associated with the encrypted sensitive information.

56. A method of securely transferring sensitive information from a remote expert data center to a programmer, the method comprising:
- generating an encryption key for distribution to the remote expert data center;
- generating a decryption key for distribution to the programmer;
- encrypting the sensitive information residing on the remote expert data center with the encryption key;
- transferring the encrypted sensitive information from the remote expert data center to the programmer; and
- decrypting the encrypted sensitive information residing on the programmer with the decryption key.

57. The method of claim 56, wherein the programmer is connected to an implantable medical device in a patient.

58. The method of claim 56, wherein the step of encrypting the sensitive information residing on the remote expert data center further comprises:
- creating a digital signature for the encrypted sensitive information.

59. The method of claim 58, wherein the step of decrypting the encrypted sensitive information residing on the programmer further comprises:
- verifying the digital signature associated with the encrypted sensitive information.

60. A system for transferring information from a programmer to a remote expert data center, the system comprising:
- means for generating an encryption key for distribution to the programmer;
- means for generating a decryption key for distribution to the remote expert data center;
- means for encrypting the sensitive information residing on the programmer with the encryption key;
- means for transferring the encrypted sensitive information from the programmer to the remote expert data center; and
- means for decrypting the encrypting sensitive information residing on the remote expert data center with the decryption key.

61. The method of claim 60, wherein the programmer is connected to an implantable medical device in a patient.

62. The system of claim 60, wherein the means for encrypting the sensitive information residing on the programmer further comprises:
- means for creating a digital signature for the encrypted sensitive information.

63. The system of claim 62, wherein the means for decrypting the encrypted sensitive information residing on the remote expert data center further comprises:
- means for verifying the digital signature associated with the encrypted sensitive information.

64. A system for transferring sensitive information from a remote expert data center to a programmer, the system comprising:
- means for generating an encryption key for distribution to the remote expert data center;
- means for generating a decryption key for distribution to the programmer;
- means for encrypting the sensitive information residing on the remote expert data center with the encryption key;
- means for transferring the encrypted sensitive information from the remote expert data center to the programmer; and
- means for decrypting the encrypting sensitive information residing on the programmer with the decryption key.

65. The system of claim 64, wherein the programmer is connected to an implantable medical device in a patient.

66. The system of claim 64, wherein the means for encrypting the sensitive information residing on the remote expert data center further comprises:
- means for creating a digital signature for the encrypted sensitive information.

67. The system of claim 66, wherein the means for decrypting the encrypted sensitive information residing on the programmer further comprises:
- means for verifying the digital signature associated with the encrypted sensitive information.

68. A remote expert data center readable medium containing instructions for controlling a remote expert data center system to perform a method for securely transferring sensitive information from a programmer to a remote expert data center, the method comprising:
- generating an encryption key for distribution to the programmer;
- generating a decryption key for distribution to the remote expert data center;
- encrypting the sensitive information residing on the programmer with the encryption key;
- transferring the encrypted sensitive information from the programmer to the remote expert data center; and
- decrypting the encrypted sensitive information residing on the remote expert data center with the decryption key.

69. A remote expert data center readable medium containing instructions for controlling a remote expert data center system to perform a method for securely transferring sensitive information from a remote expert data center to a programmer, the method comprising:
- generating an encryption key for distribution to the remote expert data center;
- generating a decryption key for distribution to the programmer;
- encrypting the sensitive information residing on the remote expert data center with the encryption key;
- transferring the encrypted sensitive information from the remote expert data center to the programmer; and
- decrypting the encrypted sensitive information residing on the programmer with the decryption key.

* * * * *